(12) United States Patent
Tas

(10) Patent No.: US 11,432,773 B2
(45) Date of Patent: Sep. 6, 2022

(54) MONITORING OF DIAGNOSTIC INDICATORS AND QUALITY OF LIFE

(71) Applicant: NEUROPATH SPRL, Louvain-la-Neuve (BE)

(72) Inventor: Benoit Yvonne Tas, Heverlee (BE)

(*) Notice: Subject to any disclaimer, the term of this patent is extended or adjusted under 35 U.S.C. 154(b) by 122 days.

(21) Appl. No.: 16/696,619

(22) Filed: Nov. 26, 2019

(65) Prior Publication Data

US 2020/0093442 A1    Mar. 26, 2020

Related U.S. Application Data

(63) Continuation-in-part of application No. 15/984,986, filed on May 21, 2018, now Pat. No. 10,485,454.

(60) Provisional application No. 62/510,749, filed on May 24, 2017.

(51) Int. Cl.
*A61B 5/00* (2006.01)
*A61B 5/11* (2006.01)

(52) U.S. Cl.
CPC ............ *A61B 5/7275* (2013.01); *A61B 5/112* (2013.01); *A61B 5/4842* (2013.01)

(58) Field of Classification Search
CPC ...... A61B 5/7275; A61B 5/112; A61B 5/4842
See application file for complete search history.

(56) References Cited

U.S. PATENT DOCUMENTS

| | | | | |
|---|---|---|---|---|
| 7,769,600 B2* | 8/2010 | Iliff | ........................ | G16H 10/60 705/2 |
| 8,326,433 B2* | 12/2012 | Blum | ..................... | A61B 34/10 607/59 |
| 8,504,392 B2* | 8/2013 | Saria | ...................... | G16H 15/00 706/45 |
| 8,566,121 B2* | 10/2013 | Ramasubramanian | ..................... | G16H 40/67 705/2 |
| 9,414,776 B2* | 8/2016 | Sillay | ...................... | G16H 30/20 |
| 9,936,916 B2* | 4/2018 | Sahin | ................... | A61B 5/0022 |
| 10,799,186 B2* | 10/2020 | Howard | ................. | G16H 70/60 |
| 10,853,455 B2* | 12/2020 | Foster | .................... | G16H 50/20 |
| 10,872,684 B2* | 12/2020 | McNutt | .................. | G16H 20/40 |
| 2004/0030672 A1* | 2/2004 | Garwin | .................. | G16H 50/70 |
| 2014/0046685 A1* | 2/2014 | Ramasubramanian | ..................... | G16H 20/10 705/2 |
| 2017/0262587 A1* | 9/2017 | Agarwal | ................. | G16H 50/20 |
| 2017/0372029 A1* | 12/2017 | Saliman | ................. | G16H 10/60 |

* cited by examiner

*Primary Examiner* — Gregory M Desire

(57) ABSTRACT

In some embodiments, the method includes a creating a plurality of session records for a subject, generating a subject progression model based on the plurality of session records, and comparing the subject progression model to a health progression model. The method further includes determining, based on the comparing the subject progression model to the health progression model, at least one progression deviation and generating a notification including an indication of the at least one progression deviation. In some embodiments, the plurality of session records include both objective data and subjective data. In some embodiments, the objective data includes one or more of body motion data captured with an RGB-D camera or RGB camera and voice data captured with a microphone. In some embodiments, the subjective data includes one or more of self-reported data from the subject and physician-reported data associated with the subject.

18 Claims, 8 Drawing Sheets

MONITORING OF DIAGNOSTIC INDICATORS AND QUALITY OF LIFE

RELATED APPLICATIONS

This application claims priority to U.S. Nonprovisional application Ser. No. 15/984,986, entitled "Systems and Methods for Markerless Tracking of Subjects", filed May 21, 2017, which claims priority to U.S. Provisional Application No. 62/510,749, entitled "Methods and System for Assessing Neurological Disease", filed May 24, 2017. The entire contents of these two applications are incorporated herein by reference.

BACKGROUND

Degenerative and neurological diseases affect millions of people worldwide and, in many cases, represent a significant degradation in a patient's quality of life over time. To track the progression of such diseases, subjects are periodically evaluated by medical professionals using established rating scales. An example rating scale for Parkinson's disease is the Movement Disorder Society unified Parkinson's disease rating scale (MDS-UPDRS). As explained below, the current examination methods for subjects suffering from degenerative and neurological diseases have significant limitations.

Currently, examinations of subjects are performed by doctors during office visits. Subjects with Parkinson's disease typically visit a doctor's office once or twice a year. Thus, their condition is only monitored 1 to 2 hours per year. This leaves about 8,765 hours per year when their condition is not being monitored.

Established rating scales (such as the MDS-UPDRS) typically include questionnaires and a series of motor exercises. Currently, a doctor watches a subject performing each of the motor exercises and then determines a rating for the subject's movement based on a series of prescribed guidelines. Many of the prescribed guidelines are subjective and open to the interpretation of the doctor performing the examination. For example, a prescribed guideline may require the doctor to differentiate between a subject walking with minor gait impairment and with substantial gait impairment. In addition, many of the prescribed guidelines require the doctor to evaluate attributes that are difficult to discern with eyeball judgement. For example, a prescribed guideline may require the doctor to differentiate between a hand tremor between 1 centimeter and 3 centimeters from a hand tremor between 3 centimeters and 5 centimeters.

Further, Parkinson's disease is a very individual disease. Every subject develops different motor and non-motors symptoms at different rates. The currently examination methods employ fixed rating scales that do not account for the symptom development of individual subjects.

SUMMARY

The disclosure provides a method of reporting health progression. In some embodiments, the method includes a creating a plurality of session records for a subject, generating a subject progression model based on the plurality of session records, and comparing the subject progression model to a health progression model. The method further includes determining, based on the comparing the subject progression model to the health progression model, at least one progression deviation and generating a notification including an indication of the at least one progression deviation. In some embodiments, the plurality of session records include both objective data and subjective data. In some embodiments, the objective data includes one or more of body motion data captured with an RGB-D camera or RGB camera and voice data captured with a microphone. In some embodiments, objective data may be captured at least in part using another type of camera or image capture device, for example a smart phone camera or a depth-sensitive image capture device. In some embodiments, objective data may be captured in part using cognitive games or other interactive activities of a patient. In some embodiments, the subjective data includes one or more of self-reported data from the subject and physician-reported data associated with the subject.

In some embodiments, the session records include data mined from one or more of the voice and the self-reported data. In some embodiments, the self-reported data is received from a portable electronic device. In some embodiments, the session records further comprise data corresponding to one or more of a location, a time stamp, and a medical professional associated with the creation of respective session records. In some embodiments, respective session records of the plurality of session records are weighed dissimilarly in generating the subject progression model.

In some embodiments, the disclosure provides a method of reporting health progression. In some embodiments, the method includes receiving health progression profiles of a plurality of subjects, selecting a cohort from among the plurality of subjects, and defining a cohort health progression model based on health progression profiles of the cohort. The progression profiles include one or more of physical health (motor data, non-motor data), social health, and emotional/mental health data. The cohort is selected based, at least in part, on a plurality of health characteristics of an individual. The method further includes determining, based on the cohort health progression model, that a parameter of a session record for the individual has deviated beyond a health progression threshold. The method further includes transmitting a notification indicating that the parameter has deviated beyond the health progression threshold and modifying the health progression model based, at least in part, on the session record.

According to some embodiments, the system may detect and/or track significant "events" in the patient data. For example, changes in sleep patterns or changes in physical, mental, or social parameters associated with a patient may be detected and tracked as noteworthy events that may be studied further. According to some embodiments, events may include deviations from a patient's baseline motor, non-motor, or emotional state. In some embodiments, events may include deviations from a prescribed care path, such as when a system detects that a patient is not getting prescribed physical activity or following a prescribed medication schedule.

According to some embodiments, significant events may be detected by analysis of other parameters. For example, a system may detect correlations between parameters. As one example, it may be considered medically significant that a patient experiences more of a specific kind of motor difficulty—or motor symptoms in general—when the patient has not slept well, as determined by self-reporting and/or sleep monitoring devices. As another example, the system may find a correlation between a patient feeling more depressed during times when the patient's social contacts are deteriorating. In some embodiments, certain such events and correlations may be specified for monitoring by a physician or patient. In some embodiments, a system may unilaterally detect events and/or correlations and choose which ones to track or report, for example by applying machine learning or other computing techniques to the gathered data.

In some embodiments, the method further includes anonymizing the subject progression model and transmitting the anonymized subject progression model to an external data source. In some embodiments, the at least one progression deviation of the subject progression model includes one or more of a speed, an acceleration, an amplitude, a number of iterations, a max height, a number of hesitations, a number of halts, a rhythm, a duration, and a stride length. In some embodiments, the health progression threshold is experimentally derived. In some embodiments, the determining includes determining that the parameter of the session record has deviated beyond the health progression threshold for a threshold period of time. In some embodiments, the modifying the health progression model includes modifying the health progression threshold.

In some embodiments, the disclosure provides a method of reporting health progression. In some embodiments, the method includes receiving health progression profiles of a plurality of subjects, receiving a session record for an individual, and providing, to a user, a set of selectable parameters. Each health progression profile includes motor, non-motor, and emotional parameters. In some embodiments, the session record includes motor, non-motor, and emotional parameters. In some embodiments, the selectable parameters include motor, non-motor, and emotional parameters. The method further includes receiving, from the user, a user selection from the set of selectable parameters. The method further includes generating an individual health progression model based on the health progression profiles and the user selection. The method further includes providing, to the user, a comparison of the first session record to the individual health progression model and providing a notification to the user in the case that a parameter of the session record deviates beyond a progression threshold.

In some embodiments, the set of selectable parameters is provided to a user at a portable electronic device. In some embodiments, the session record includes data corresponding to one or more of a location, a time stamp, and a medical professional associated with the creation of the session record. In some embodiments, the notification includes one or more of the parameter, the session record, and the progression threshold.

In some embodiments, the disclosure provides a method of reporting health progression. In some embodiments, the method includes receiving health progression profiles of a plurality of subjects, receiving a session record for an individual, and selecting a cohort from among the plurality of subjects based on the session record. In some embodiments, each progression profile includes health progression parameters having respective temporal components. In some embodiments, the session record includes health progression parameters. The method further includes generating a health progression model based on health progression profiles of the cohort and detecting a deviation of a health progression parameter of the session record beyond a corresponding health progression threshold of the health progression model. The method further includes identifying one or more corresponding health progression profiles which include the deviation, receiving an improvement strategy of the one or more corresponding progression profiles, and providing the improvement strategy to a user. In some embodiments, the user is a medical professional associated with the individual. In some embodiments, the method further includes providing the improvement strategy with a request for authorization to the user, such as the medical professional.

Other aspects and embodiments will become apparent by consideration of the detailed description and accompanying drawings.

Figure 1:
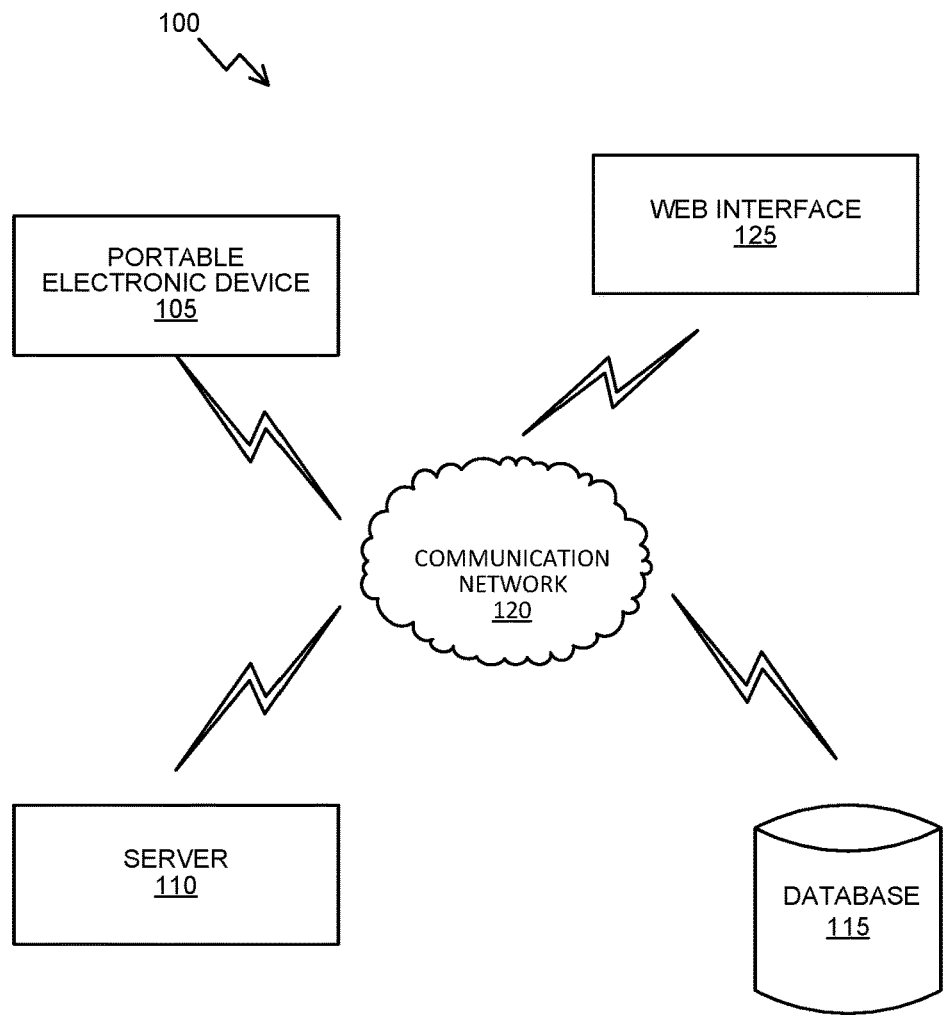
FIG. 1 is a health progression reporting system, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments illustrated.

The apparatus and method components have been represented where appropriate by conventional symbols in the drawings, showing only those specific details that are pertinent to understanding various embodiments so as not to obscure the disclosure with details that will be readily apparent to those of ordinary skill in the art having the benefit of the description herein.

DETAILED DESCRIPTION

Before any embodiments are explained in detail, it is to be understood that no embodiment is necessarily limited in its application to the details of construction and the arrangement of components set forth in the following description or illustrated in the following drawings. Other embodiments are possible and embodiments described are capable of being practiced or of being carried out in various ways.

It should also be noted that a plurality of different structural components may be utilized to implement the disclosure. Furthermore, and as described in subsequent paragraphs, the specific configurations illustrated in the drawings are intended to exemplify certain embodiments. Alternative configurations are possible.

For ease of description, the example systems presented herein may be illustrated with a single exemplar of each of their component parts. Some examples may not describe or illustrate all components of the systems. Other example embodiments may include more or fewer of each of the illustrated components, may combine some components, or may include additional or alternative components. FIG. 1 is a diagram of one example embodiment of a health progression reporting system 100. In the embodiment illustrated in FIG. 1, the health progression reporting system 100 includes an portable electronic device 105, a server 110, a database 115, a communication network 120, and a web interface 125.

The portable electronic device 105 illustrated in FIG. 1 includes an electronic processor (for example, a microprocessor), a memory, a transceiver, and a user interface. The electronic processor, the memory, as well as the other various modules are coupled by a bus, or are coupled directly, by one or more additional control or data buses, or a combination thereof. The memory may include read only memory (ROM), random access memory (RAM), other non-transitory computer-readable media, or a combination thereof. The electronic processor is configured to retrieve program instructions and data from the memory and execute, among other things, instructions to perform the methods described herein. The transceiver transmits signals to the communication network 120 and receives signals from the communication network 120.

Signals may include, for example, information, data, serial data, data packets, analog signals, or a combination thereof. The transceiver can be coupled to one or more separate transceivers via wires, fiber, wirelessly, or a combination thereof. In some embodiments, the transceiver includes separate transmitters and receivers. The user interface is included to control the portable electronic device or the operation of the health progression reporting system 100 as a whole. The user interface can include any combination of digital and analog input devices required to achieve a desired level of control for the system 100. In some embodiments, the user interface includes a touch sensitive interface. For example, in some embodiments, the display screen is a touch-screen display that receives user input using detected physical contact (for example, detected capacitance or resistance). Based on the user input, the display screen outputs signals to the electronic processor which indicate positions on the display screen currently being selected by physical contact. Alternatively or in addition, the user interface receives user input from a plurality of input devices such as a keyboard, a mouse, a trackpad, the microphone, and the like. In some constructions, the user interface is separated from the portable electronic device 105.

The communication network 120 may be a wired network, a wireless network, or both. All or parts of the communication network 120 may be implemented using various networks, for example, a cellular network, the Internet, a Bluetooth™ network, a wireless local area network (for example, Wi-Fi), a wireless accessory Personal Area Networks (PAN), cable, an Ethernet network, satellite, a machine-to-machine (M2M) autonomous network, and a public switched telephone network. The portable electronic device 105, the server 110, the web interface 125, and the other various components of the health progression reporting system 100 communicate with each other over the communication network 120 using suitable wireless or wired communication protocols. In some embodiments, communications with other external devices (not shown) occur over the communication network 120.

In some embodiments, the web interface 125 may provide an easily accessible interface for both subjects and physicians to interact with the health progression reporting system 100 at any device connected to the communication network 120. The health progression reporting system 100 illustrated in FIG. 1 is provided as one example of such a system. The methods described herein may be used with health progression reporting systems with fewer, additional, or different components in different configurations than the health progression reporting system 100 illustrated in FIG. 1. For example, in some embodiments, the health progression reporting system 100 includes fewer or additional portable electronic devices, fewer or additional servers, fewer or additional web interfaces, and fewer or additional databases.

Figure 2:
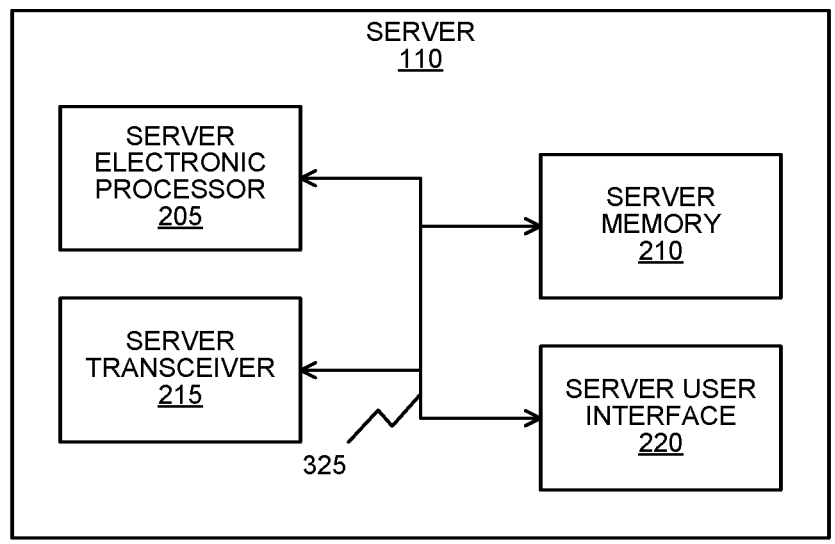
FIG. 2 is a diagram of a server included in the health progression reporting system of FIG. 1, in accordance with some embodiments.

FIG. 2 is a diagram of one example embodiment of the server 110. In the example illustrated, the server 110 includes a server electronic processor 205, server memory 210, a server transceiver 215, and a server user interface 220. The server electronic processor 205, the server memory 210, as well as the other various modules are coupled by a bus 225, or are coupled directly, by one or more additional control or data buses, or a combination thereof. In other embodiments, the server 110 may include fewer or additional components in configurations different from that illustrated in FIG. 2.

The server memory 210 stores program instructions and data. The server memory 310 may include combinations of different types of memory, including the various types of memory described above with respect to the memory 225 included in the portable electronic device 105. The server electronic processor 205 retrieves program instructions from the server memory 210 and executes the instructions to perform a set of functions including all or part of the methods described herein. The server transceiver 215 transmits signals to and receives signals from the portable electronic device 105 and the other components included in the health progression reporting system 100, such as through the communication network 120 or directly. The server user interface 220 includes any combination of digital and analog input devices required to achieve a desired level of control for the server 110. For example, the server user interface 220 can include a computer having a display and input devices, a display, a keyboard, a mouse, speakers, and the like.

In some embodiments, the database 115 may include components or combinations of different components, including all or some of the various components described above with respect to the server 110.

Figure 3:
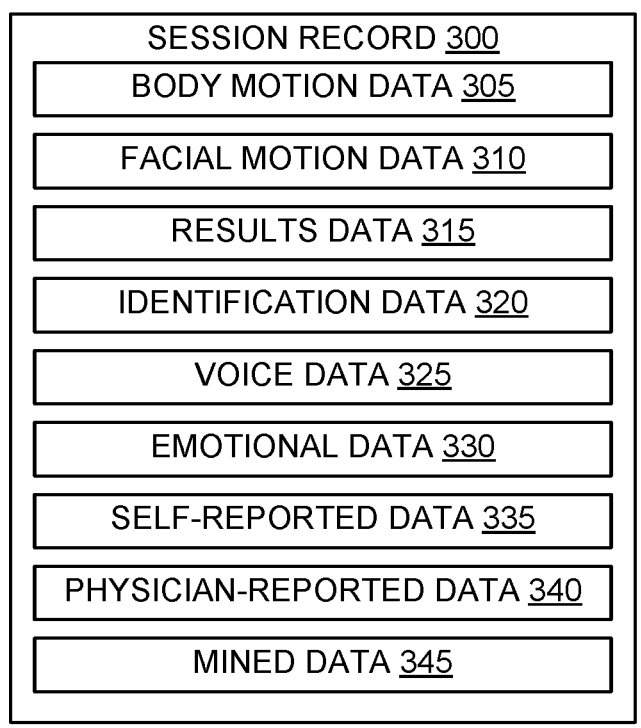
FIG. 3 is a diagram of a session record, in accordance with some embodiments.

FIG. 3 is a diagram of one example embodiment of a session record 300 for a subject. In the example illustrated in FIG. 3, the session record 300 includes body motion data 305, facial motion data 310, result data 315, identification data 320, voice data 325, emotional data 330, self-reported data 335, physician-reported data 340, and mined data 34. In other embodiments, a session record may include fewer or additional components in configurations different from that illustrated in FIG. 3.

The body motion data 305 includes all (or any portion) of the sets of 3D coordinates for the plurality of body joints captured by an RGB-D or infrared camera 205. In some embodiments, facial motion data 310 for the subject's face is captured by the RGB-D camera. The result data 315 includes, among other things, the rating for a motor exercise, a set of attributes for movements of the subject's body, the movements of the subject's body, or a combination thereof. The identification data 320 includes, among other things, a subject identifier, a motor exercise identifier, a session identifier, or a combination thereof. The subject identifier identifies the subject performing the motor exercise. The subject identifier may include, for example, a unique identification number assigned to the subject, the subject's name, the subject's date of birth, the subject's gender, the subject's telephone number, the subject's e-mail address, or a combination thereof. The session identifier may include, for example, a unique identification number for the session, a time stamp, or both. Subjects with neurological diseases, such as Parkinson's disease, often experience decreased motor functionality over time. The decreased motor functionality can be tracked by comparing measured attributes of motor exercises from different session records. In addition, subjects with neurological diseases typically take medication to limit mobility symptoms. The session records may also be used to determine the effect of different medications on the mobility of a patient.

Returning to FIG. 3, the audio data 325 includes, among other things, all (or any portion) of the sound recorded from the subject during a session. The emotional data 330 includes data indicating non-movement symptoms of the subject. For example, questionnaires may be used to capture feedback from a subject regarding the subject's quality of life.

Additionally, the self-reported data includes data submitted to the system 100 by the subject. In some embodiments, the self-reported data includes data shared with the emotional data 330. The physician-reported data 340 includes data submitted to the system 100 by one or more medical professionals associated with the subject. The mined data 345 includes data extracted from one or more other aspects of the session record 300. For example, the mined data 345 may include data indicative of a change in emotional state of the subject based on data from the voice data 325, or the application of neurolinguistics processing techniques to the self-reported data 335.

In some embodiments, the server 110 includes (or implements) a machine learning engine that can assign a subject progression model to a subject by evaluating a plurality of session records for the subject. The machine learning engine evaluates data within the respective session records to train a classifier of the machine learning engine. The machine learning engine models the respective progressions collected from various subjects in order to differentiate between different subjects, such as control subjects and cohort subjects. The health progression reporting system 100 can use the machine learning engine to predict the health progression of a subject in substantially real time using data captured by the health progression reporting system 100 including, among other things, body motion data 305, facial motion data 310, result data 315, voice data 325, emotional data 330, mined data 345, or a combination thereof.

Figure 4:
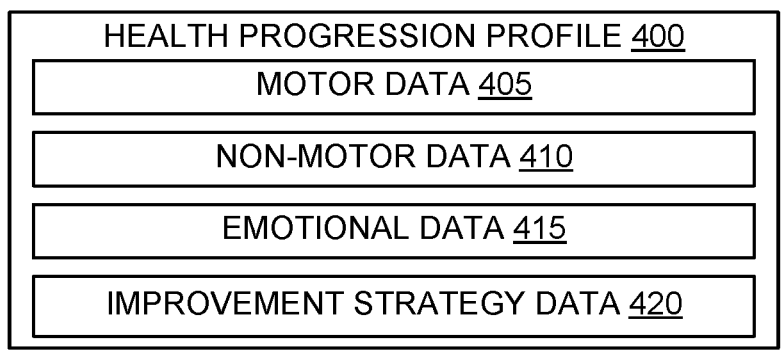
FIG. 4 is a diagram of a health progression profile, in accordance with some embodiments.

FIG. 4 is a diagram of one example embodiment of a health progression profile 400. In the example illustrated in FIG. 4, the health progression profile 400 includes motor data 405, non-motor data 410, emotional data 415, and improvement strategy data 420. In other embodiments, a health progression profile 400 may include fewer or additional components in configurations different from that illustrated in FIG. 4.

In one embodiment, the motor data 405 comprises data related to tremors, rigidity, postural instability, bradykinesia, shuffling gait, micrographia, mask like expressions, and speech difficulties. In some embodiments, non-motor data 410 comprises data related to olfactory disturbance, constipation, orthostatic hypotension, insomnia, excessive daytime somnolence, and rapid eye movement sleep behavior disorder (RBD). In some embodiments, emotional data 415 includes such concepts as depression and anxiety. In some embodiments, the improvement strategy data 420 includes various treatment plans, such as pharmaceutical prescriptions, exercise regiments, nutritional targets, cognitive or emotional therapy, or any other treatment plan aimed at improving a subject's outcome.

Figure 5:
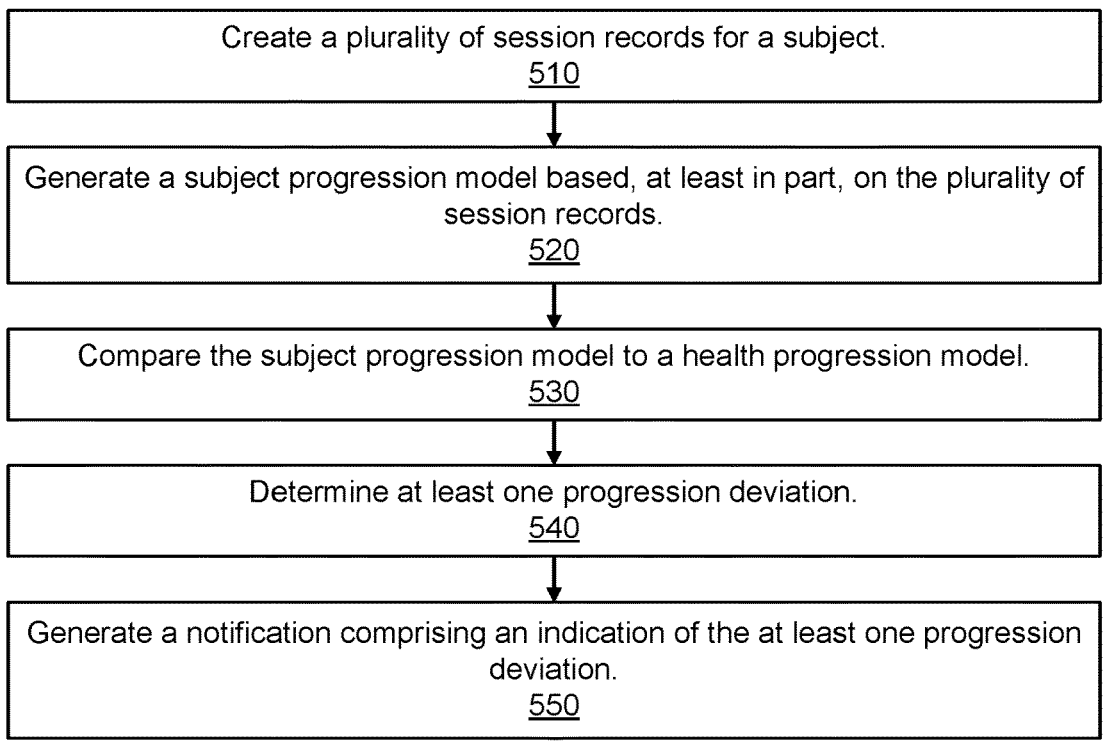
FIG. 5 is a flowchart of a method of reporting a health progression, in accordance with some embodiments.

FIG. 5 is a flow diagram of a method of reporting health progression 500. At step 510, a plurality of session records is created for a subject. In some embodiments, a session record comprises a medical check-up or physical assessment in the context of a hospital or medical facility. In other embodiments, a session record comprises a movement analysis in a subject's home. In some embodiments, the plurality of session records is created substantially simultaneously, such as during in intake of a patient's medical records. Alternatively, the plurality of session records may be created over one or more periods of time. In some embodiments, a session record comprises self-reported data. Accordingly, a session record may comprise objective data and/or subjective data. For example, one or more session records may include objective data such as body motion data captured with an RGB-D camera or an accelerometer associated with a subject. Alternatively, or in addition, one or more session records may comprise objective data such as voice data associated with the subject, such as captured with a microphone. Further, one or more session records may comprise subjective data such as self-reported data from the subject. One or more session records may comprise subjective data such as physician-reported data associated with the subject. Accordingly, the plurality of session records comprises both objective and subjective data.

At step 520, a subject progression model is generated based, at least in part, on the plurality of session records. For example, the session records may comprise data captured for a particular health characteristic or other parameter captured at different times. Accordingly, the temporal data corresponding to the particular health characteristic or other parameter is used to generate progression of the particular health characteristic or other parameter associated with the subject. At step 530, the subject progression model is compared to a health progression model. For example, a health progression model may include experimentally derived data of progressions of a particular health characteristic or other parameter. Further, various analytical data may be included in or derived from the health progression model. For example, analytical data may comprise an expected variability or variance in the progression of a health characteristic or other parameter. Accordingly, the heath progression model may comprise an expected progression of one or more health characteristics or other parameters having expected ranges or thresholds.

At step 540, at least one progression deviation is determined based on the comparison of the subject progression model to the health progression model. For example, in the case that a health characteristic of the subject deviates beyond an expected range or threshold of a corresponding health characteristic of the health progression model. At step 550, a notification comprising an indication of the at least one progression deviation is generated.

According to some embodiments, the system may detect and/or track significant "events" in the patient data. For example, changes in sleep patterns or changes in physical, mental, or social parameters associated with a patient may be detected and tracked as noteworthy events that may be studied further. According to some embodiments, events may include deviations from a patient's baseline motor, non-motor, or emotional state. In some embodiments, events may include deviations from a prescribed care path, such as when a system detects that a patient is not getting prescribed physical activity or following a prescribed medication schedule.

According to some embodiments, significant events may be detected by analysis of other parameters. For example, a system may detect correlations between parameters. As one example, it may be considered medically significant that a patient experiences more of a specific kind of motor difficulty—or motor symptoms in general—when the patient has not slept well, as determined by self-reporting and/or sleep monitoring devices. As another example, the system may find a correlation between a patient feeling more depressed during times when the patient's social contacts are deteriorating. In some embodiments, certain such events and correlations may be specified for monitoring by a physician or patient. In some embodiments, a system may unilaterally detect events and/or correlations and choose which ones to track or report, for example by applying machine learning or other computing techniques to the gathered data.

Figure 6:
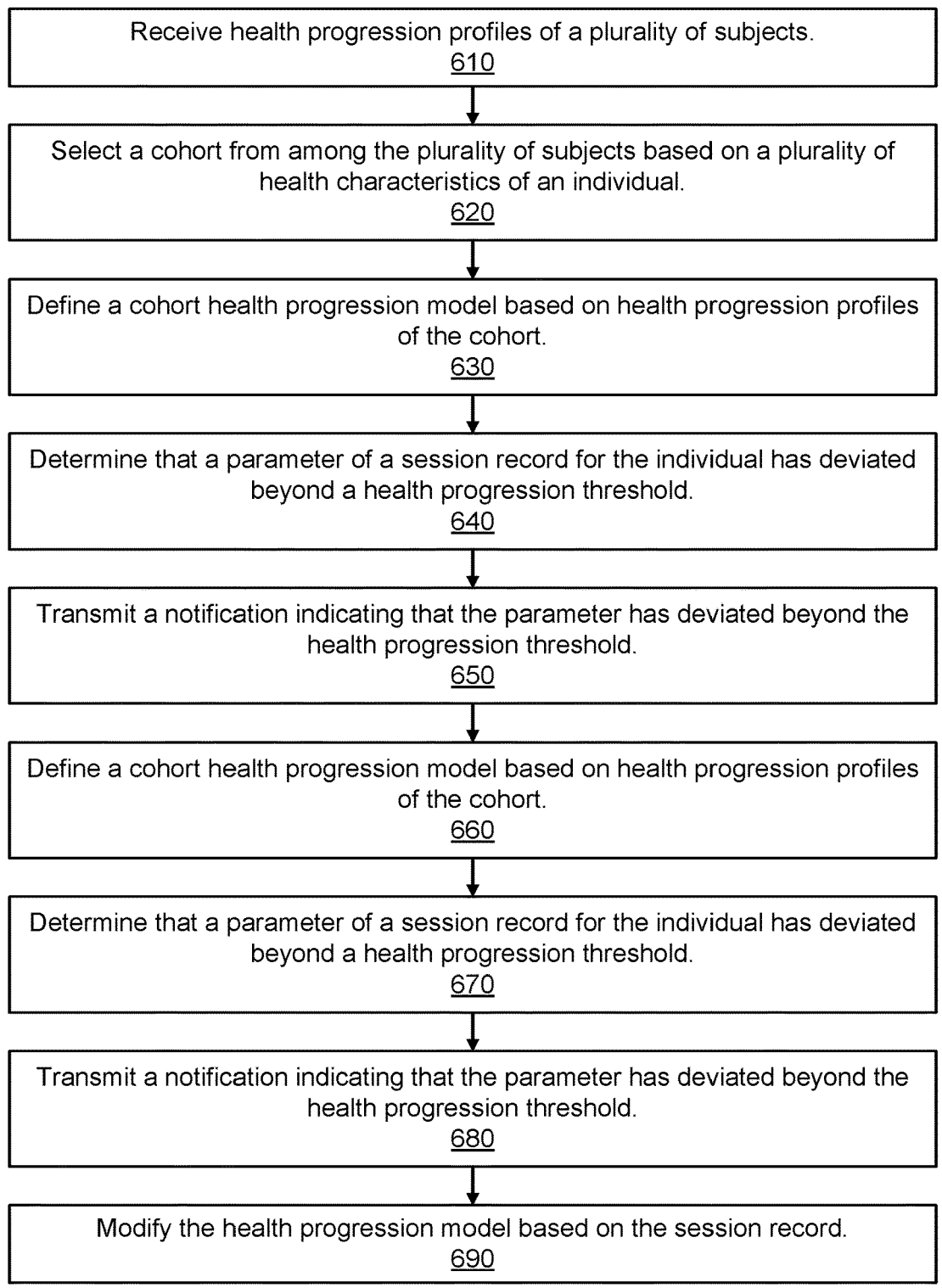
FIG. 6 is a flowchart of a method of reporting a health progression related to a cohort of a subject, in accordance with some embodiments.

FIG. 6 is a flow diagram of a method 600 of reporting health progressions. At step 610, health progression profiles of a plurality of subjects are received. Data of the health progression profiles may be acquired from a remote server including data from, for example, a plurality of research publications, meta-analyses, or health records. The health progression profiles include one or more of motor data, non-motor data, and emotional data. In some embodiments, motor data comprises data related to tremors, rigidity, postural instability, bradykinesia, shuffling gait, micrographia, mask like expressions, and speech difficulties. In some embodiments, non-motor data comprises data related to olfactory disturbance, constipation, orthostatic hypotension, insomnia, excessive daytime somnolence, and rapid eye movement sleep behavior disorder (RBD). In some embodiments, emotional data includes such concepts as depression and anxiety.

At step 620, a cohort from among the plurality of subjects is selected based, at least in part, on a plurality of health characteristics of an individual. For example, selection of a cohort may be based on any desired characteristic, such as physical characteristics, behavioral characteristics, or socio-economic or environmental characteristics associated with a subject. For example, the sex of the subject may be used to assist in selection of a cohort. Alternatively, or in addition, a level of physical activity may be used to assist in selection of a cohort. Similarly, socioeconomic or environmental characteristics may be used to assist in selection of a cohort, as such characteristics can impact the health progression of a subject. Although a plurality of health characteristics of the individual influence the selection of the cohort, not all health characteristics need be considered in selection of the cohort. In some embodiments, a cohort comprises all subjects within the plurality of subjects having similar health characteristics as the individual. In other embodiments, the cohort comprises fewer than all subjects having similar health characteristics as the individual. In yet further embodiments, the cohort comprises more than all subjects having similar health characteristics as the individual. Accordingly, the cohort can be narrowed or broadened as desired.

At step 630, a cohort health progression model is defined based, at least in part, on health progression profiles of the cohort. At step 640, a parameter of a session record for the individual is determined to have deviated beyond a health progression threshold. For example, a threshold of a parameter or characteristic may be experimentally derived, such as a stride speed. Alternatively, a threshold of a parameter or characteristic may be user-defined, such as by a medical professional. For example, the sensitivity of a health progression model may be influence by the sample size of the cohort used to generate the cohort health progression model. In addition to merely exceeding a threshold, a deviation may be determined to have occurred in the case that one or more parameters exceeds a threshold for a period of time. Further, the period of time may be based, at least in part, on the amount by which the parameter exceeds the threshold. Accordingly, determination quality may be improved.

At step 650, a notification indicating that the parameter has deviated beyond the health progression threshold is transmitted. For example, the notification may be transmitted to a portable electronic device associated with an individual. At step 660, the health progression model is modified based, at least in part, on the session record. At the very least, a cohort health progression model may be modified to include the session record. Further, a modification of the cohort health progression model may comprise modifying a health progression threshold for one or more parameters.

Figure 7:
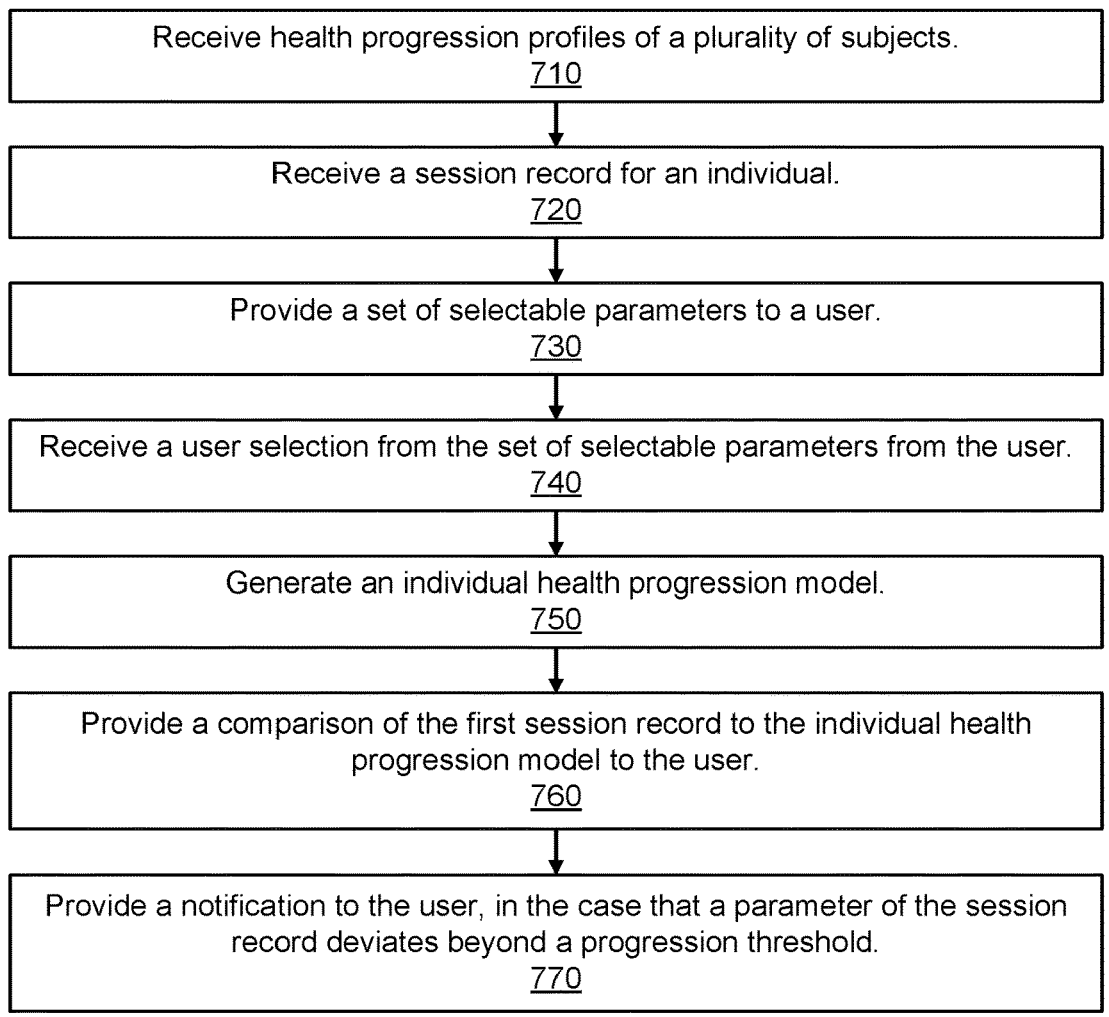
FIG. 7 is a flowchart of a method of reporting a health progression comprising user interactions, in accordance with some embodiments.

FIG. 7 is a flow diagram of a method 700 of reporting health progression. At step 710, health progression profiles of a plurality of subjects are received. A health progression profile may be received from an external data source, such as a remote server, and may include a plurality of health records. At step 720, a session record for an individual is received. In some embodiments, the session record includes motor, non-motor, and emotional parameters. At step 730, a set of selectable parameters is provided to a user. For example, the selectable parameters may include a plurality of health characteristics associated with the individual. In some embodiments, the selectable parameters include motor parameters, non-motor parameters, and emotional parameters. The set of selectable parameters is provided to the user via a user interface, such as a GUI of an electronic devices, such as a laptop or smartphone. The selectable parameters may comprise a set of parameters selected by default based on, for example, a preference set by the user.

At step 740 a user selection from the set of selectable parameters from the user is received. The user selection may comprise all of the set of selectable parameters. Alternatively, the user selection may comprise fewer than all of the set of selectable parameters. At step 750, an individual health progression model is generated based, at least in part, on the health progression profiles and the user selection. At step 760, a comparison of the first session record to the individual health progression model is provided to the user. The comparison of the first session record to the individual health progression model may be provided to the user at the same electronic device from which the selectable parameters were received, or may be provided at a different device as desired. At step 770, a notification to the user is provided, in the case that a parameter of the session record deviates beyond a progression threshold. The notification may be provided to the user at the same electronic device from which the selectable parameters were received, or may be provided at a different device as desired. The notification may comprise various alerts, such as auditory, visual or haptic alerts. The notification may further comprise one or more of the parameter, the session record, the progression threshold, and other data associated with the individual.

Some health progression parameters may include degradation or improvement in motor parameters, such as stride length, speed, or freezing of gait. Health progression parameters may also include degradation or improvement in non-motor parameters, such as insomnia or excessive daytime somnolence. For example, movement of a user within their home may be captured for indications of insomnia or excessive daytime somnolence Similarly, health progression parameters may include data related to depression and anxiety. Further, a health progression parameter may include a combination of a plurality of parameters. For example, in the case that a health progression parameter comprises a motor parameter including stride length, speed, and gait parameters, a deviation of the motor parameter beyond a progression threshold may be determined even in the case that fewer than all of the stride length, speed, and gait parameters deviated beyond respective progression thresholds.

Figure 8:
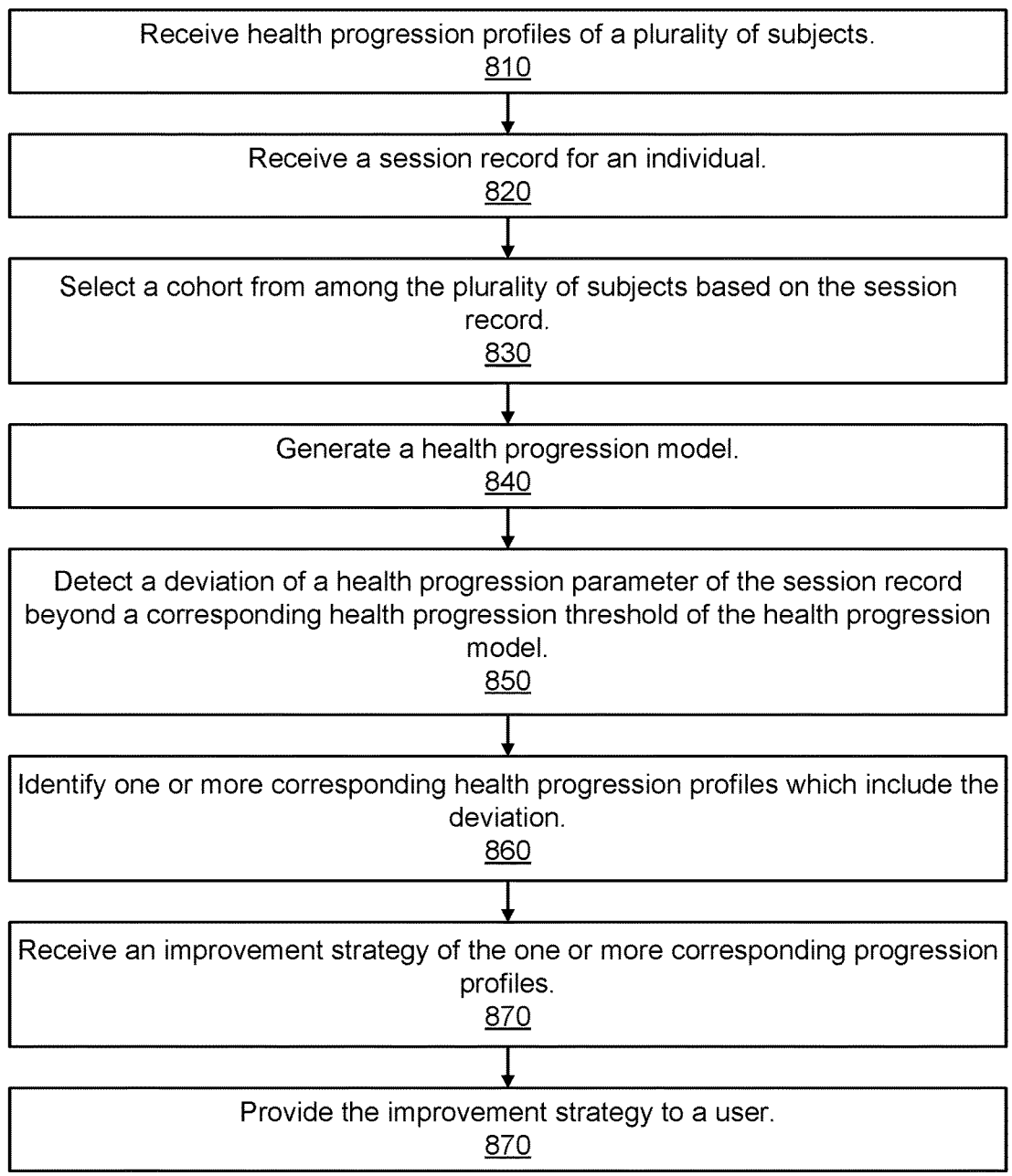
FIG. 8 is a flowchart of a method of reporting a health progression related to an improvement strategy, in accordance with some embodiments.

FIG. 8 is a flow diagram of a method of reporting health progression 800. At step 810 of the method 800, health progression profiles of a plurality of subjects are received. At step 820, a session record for an individual is received. At step 830, a cohort from among the plurality of subjects is selected based on the session record. At step 840, a health progression model is generated. At step 850, a deviation of a health progression parameter of the session record is detected. For example, the detecting may include detecting that the health progression parameter of the session record has deviated beyond a corresponding health progression threshold of the health progression model.

At step 860, one or more corresponding health progression profiles are identified. For example, one or more corresponding health progression profiles may include a substantially similar deviation as the detected deviation. A corresponding health progression profile may be selected based at least in part on any desired characteristic, for example physical characteristics, behavioral characteristics, or socioeconomic or environmental characteristics, a corresponding health progression profile including a similar deviation may be selected based on, for example, a similarity in age and sex between an individual and one or more of the health progression profiles. At step 870, an improvement strategy of the one or more corresponding progression profiles is received. Improvement strategies includes various treatment plans, such as pharmaceutical prescriptions, exercise regiments, nutritional targets, cognitive or emotional therapy, or any other treatment plan aimed at improving a subject's outcome. The improvement strategy may be included in a health progression profile of a subject, such as a prescribed exercise regimen.

At step 880, the improvement strategy is provided to a user. The improvement strategy may be provided to a medical professional associated with the individual. For example, the improvement strategy may be suggested to the medical professional in conjunction with the one or more corresponding health progression profiles from which the improvement strategy was identified. Accordingly, decision-making by the medical professional may be improved. Alternatively, or in addition, an improvement strategy may be provided to the individual or family member, such as at a display device within the individual's home For example, in the case that the improvement strategy comprises an exercise or movement regimen, the improvement strategy may be provided to an interactive gaming system in the individual's home. Accordingly, subject participation and health outcomes may be improved.

In the case that the improvement strategy is provided to a medical professional, the improvement strategy may be provided with a request for authorization. Accordingly, the medical professional may authorize the improvement strategy, which may subsequently be provided to the individual. In the case that the improvement strategy is provided to the individual, the individual may respond, for example, to opt-in to the improvement strategy, or provide feedback to the medical professional.

What is claimed is:

1. A method of reporting health progression, comprising:
    creating a plurality of session records for a subject, the plurality of session records comprising both objective data and subjective data, wherein the objective data comprises one or more of:
        body motion data captured with an active 3D camera or RGB camera, and
        voice data captured with a microphone, and
    wherein the subjective data comprises one or more of:
        self-reported data from the subject, and
        physician-reported data associated with the subject;
    generating a subject progression model based, at least in part, on the plurality of session records;
    comparing the subject progression model to a health progression model;
    determining, based on the comparing the subject progression model to the health progression model, at least one progression deviation; and
    generating a notification comprising an indication of the at least one progression deviation.

2. The method of reporting health progression of claim 1, wherein the session records include data mined from one or more of the voice data and the self-reported data.

3. The method of reporting health progression of claim 1, wherein the self-reported data is received from a portable electronic device.

4. The method of reporting health progression of claim 1, wherein the session records further comprise data corresponding to one or more of: a location where the session record was created, a time stamp of when the session records was created, and a medical professional associated with the creation of respective session records.

5. The method of reporting health progression of claim 1, wherein respective session records of the plurality of session records are weighed dissimilarly in generating the subject progression model.

6. A method of reporting health progression, comprising:
    receiving health progression profiles of a plurality of subjects, the progression profiles comprising both motor data and emotional data;
    selecting a cohort from among the plurality of subjects based, at least in part, on a plurality of health characteristics of an individual;
    defining a cohort health progression model based on health progression profiles of the cohort;
    determining, based at least in part on the cohort health progression model, that a parameter of a session record for the individual has deviated beyond a health progression threshold;
    transmitting a notification indicating that the parameter has deviated beyond the health progression threshold; and
    modifying the health progression model based, at least in part, on the session record.

7. The method of reporting health progression of claim 6, further comprising:
    anonymizing the subject progression model; and
    transmitting the anonymized subject progression model to an external data source.

8. The method of reporting health progression of claim 6, wherein the at least one progression deviation of the subject progression model comprises one or more of: a speed, an acceleration, an amplitude, a number of iterations, a max height, a number of hesitations, a number of halts, a rhythm, a duration, and a stride length.

9. The method of reporting health progression of claim 6, wherein the health progression threshold is experimentally derived.

10. The method of reporting health progression of claim 6, wherein determining further comprises determining that the parameter of the session record has deviated beyond the health progression threshold for a threshold period of time.

11. The method of reporting health progression of claim 6, where in the modifying the health progression model comprises modifying the health progression threshold.

12. A method of reporting health progression, comprising:
receiving health progression profiles of a plurality of subjects, each health progression profile comprising both motor data and emotional parameters;
receiving a session record for an individual, the session record comprising motor, non-motor, and emotional parameters;
providing, to a user, a set of selectable parameters comprising motor, non-motor, and emotional parameters;
receiving, from the user, a user selection from the set of selectable parameters;
generating, based at least in part on the health progression profiles and the user selection, an individual health progression model;
providing, to the user, a comparison of the first session record to the individual health progression model; and
providing a notification to the user, in the case that a parameter of the session record deviates beyond a progression threshold.

13. The method of claim 12, wherein the set of selectable parameters is provided to a user at a portable electronic device.

14. The method of claim 12, wherein the session record further comprises data corresponding to one or more of: a location where the session record was created, a time stamp of when the session records was created, and a medical professional associated with the creation of the session record.

15. The method of claim 12, wherein the notification further comprises one or more of the parameter, the session record, and the progression threshold.

16. A method of reporting health progression, comprising:
receiving health progression profiles of a plurality of subjects, each progression profile comprising health progression parameters having respective temporal components;
receiving a session record for an individual, the session record comprising health progression parameters;
selecting a cohort from among the plurality of subjects based, at least in part, on the session record;
generating, based at least in part on health progression profiles of the cohort, a health progression model;
detecting a deviation of a health progression parameter of the session record beyond a corresponding health progression threshold of the health progression model;
identifying one or more corresponding health progression profiles which include the deviation;
receiving an improvement strategy of the one or more corresponding progression profiles; and
providing the improvement strategy to a user.

17. The method of claim 16, wherein the user is a medical professional associated with the individual.

18. The method of claim 17, wherein the providing the improvement strategy to the user further comprises providing a request for authorization to the user.

* * * * *